(12) United States Patent
Zavalloni et al.

(10) Patent No.: US 12,391,502 B2
(45) Date of Patent: Aug. 19, 2025

(54) METHOD AND APPARATUS FOR FEEDING A PRODUCTION LINE OF ABSORBENT SANITARY ARTICLES WITH A LAYER OF A VIRGIN MULTILAYER TAPE

(71) Applicant: GDM S.p.A., Bologna (IT)

(72) Inventors: Alessandro Zavalloni, Bologna (IT); Federico Toscani, Bologna (IT); Eros Rossi, Bologna (IT)

(73) Assignee: GDM S.P.A., Bologna (IT)

( * ) Notice: Subject to any disclaimer, the term of this patent is extended or adjusted under 35 U.S.C. 154(b) by 0 days.

(21) Appl. No.: 18/811,161

(22) Filed: Aug. 21, 2024

(65) Prior Publication Data

US 2025/0091830 A1    Mar. 20, 2025

(30) Foreign Application Priority Data

Sep. 15, 2023   (IT) .......................... 102023000018960

(51) Int. Cl.
*B65H 19/18*    (2006.01)

(52) U.S. Cl.
CPC . *B65H 19/1852* (2013.01); *B65H 2701/1924* (2013.01); *Y10T 156/11* (2015.01)

(58) Field of Classification Search
CPC ........ B65H 19/1852; B65H 2701/1924; Y10T 156/11; Y10T 156/1168; B32B 38/0004
See application file for complete search history.

(56) References Cited

U.S. PATENT DOCUMENTS

| 2004/0019400 A1 | 1/2004 | Popp et al. |
| 2004/0060641 A1 | 4/2004 | Ward et al. |
| 2005/0241774 A1 | 11/2005 | Hart et al. |
| 2012/0152466 A1* | 6/2012 | Homoelle ................ D04H 1/42 |
| | | 156/714 |
| 2019/0071590 A1* | 3/2019 | Hamazaki .................. C09J 7/40 |

(Continued)

FOREIGN PATENT DOCUMENTS

| JP | 2005-533696 A | 11/2005 |
| JP | 2015-086325 A | 5/2015 |

(Continued)

OTHER PUBLICATIONS

Machine Translation JP2016108096 (Year: 2016).*

(Continued)

*Primary Examiner* — George R Koch
*Assistant Examiner* — Christopher C Caillouet
(74) *Attorney, Agent, or Firm* — DILWORTH IP, LLC

(57) ABSTRACT

A method for feeding a production line of absorbent sanitary articles with a layer of a virgin multilayer tape including providing a head free end of the virgin multilayer tape partially unwound from a respective virgin spool; providing a tail free end of a multilayer tape in use; applying a first connecting element on a first layer of the virgin multilayer tape and on a first layer of the multilayer tape in use at the head free end and tail free end; applying a second connecting element on a second layer of the virgin multilayer tape and on a second layer of the multilayer tape in use at the head free end and tail free end; pulling the first layer of the virgin multilayer tape in a first direction; pulling the second layer of the virgin multilayer tape in a second direction.

9 Claims, 7 Drawing Sheets

(56) References Cited

U.S. PATENT DOCUMENTS

2021/0371226 A1   12/2021   Perego

FOREIGN PATENT DOCUMENTS

JP   2016-108096 A   6/2016
JP   2019-038634 A   3/2019

OTHER PUBLICATIONS

Search Report issued in Italian Patent Application No. 102023000018960, issued Mar. 21, 2024, 9 pages.
Office Action received for Japanese Patent Application No. 2024-103466, mailed on Feb. 12, 2025, 7 pages (4 pages of English Translation and 3 pages of Original Document).

\* cited by examiner

METHOD AND APPARATUS FOR FEEDING A PRODUCTION LINE OF ABSORBENT SANITARY ARTICLES WITH A LAYER OF A VIRGIN MULTILAYER TAPE

FIELD OF THE INVENTION

The present invention relates to a method and an apparatus for feeding a production line of absorbent sanitary articles with a layer of a virgin multilayer tape.

BACKGROUND

Absorbent sanitary articles are for example sanitary pads for women, baby diapers, diapers and pads for people suffering from incontinence and the like. In the following description, reference will be made to the non-limiting example of the sanitary pads for women.

Structurally, a sanitary pad for women comprises a lower layer (i.e. backsheet) and an upper layer (i.e. topsheet) overlapped and joined together and an absorbent core interposed between the lower layer and the upper layer. The sanitary pad for women further comprises two flaps, which may be formed by the lower layer and/or by the upper layer. The flaps can be folded when the pad is applied to an underwear worn by the user to improve the stability of the pad.

One or more adhesive portions are placed on the lower layer to secure the pad to the underwear worn by the user. The adhesive portions are usually arranged at a central portion of the pad and on the flaps.

Typically, the adhesive portions comprise a glue layer applied on the lower layer and a covering sheet (i.e. release paper) overlapping the glue layer. The covering sheet is typically made of paper and can be removed when the pad is applied in order to expose the glue. The covering sheet is configured so that when it is removed the glue remains on the lower layer of the pad.

The Applicant has observed that in some processes for the production of the absorbent sanitary articles at least some of the layers or sheets mentioned above can be obtained starting from multilayer tapes wound in respective spools. In this case, it is necessary to separate the various layers/sheets of each multilayer tape unwound from the respective spool so as to feed the production line of the absorbent sanitary articles with only one of said layers/sheets, hereinafter referred to as the "layer of interest".

The Applicant has also observed that in the aforesaid processes, once a spool of multilayer tape is depleted, it is necessary to unwind a new multilayer tape from a new virgin spool in order to continue feeding the layer of interest to the production line.

SUMMARY

The Applicant has perceived that it is possible to feed the layer of interest of the new multilayer tape unwound from the new virgin spool by joining the new multilayer tape to the multilayer tape in use.

The Applicant has also perceived that, in order to separate two layers of the new multilayer tape, hereinafter referred to as the first layer and the second layer, it is possible to join together both the first layers of the multilayer tape in use and of the virgin multilayer tape, and the second layers of the multilayer tape in use and of the virgin multilayer tape, in such a way that by pulling the two layers of the multilayer tape in use in divergent directions, the two layers of the virgin multilayer tape are also pulled in divergent directions, thereby separating one another.

The present invention therefore relates, in a first aspect thereof, to a method for feeding a production line of absorbent sanitary articles with a layer of a virgin multilayer tape.

Preferably, a head free end of said virgin multilayer tape partially unwound from a respective virgin spool is provided.

Preferably, a tail free end of a multilayer tape in use is provided.

Preferably, a first connecting element is applied on a first layer of the virgin multilayer tape and on a first layer of the multilayer tape in use at said head free end and tail free end.

Preferably, a second connecting element is applied on a second layer of the virgin multilayer tape and on a second layer of the multilayer tape in use at said head free end and tail free end.

Preferably, the first layer of said virgin multilayer tape is pulled in a first direction by making the first layer of the multilayer tape in use and the first connecting element advance in the first direction.

Preferably, the second layer of said virgin multilayer tape is pulled in a second direction by making the second layer of the multilayer tape in use and the second connecting element advance in the second direction.

Preferably, the second direction is divergent from the first direction.

By applying the first connecting element and the second connecting element, the first layers of the multilayer tape in use and of the virgin multilayer tape are joined.

By applying the second connecting element, the second layers of the multilayer tape in use and of the virgin multilayer tape are joined.

By pulling the first layer of the multilayer tape in use and the second layer of the multilayer tape in use in divergent directions, the first layer of the virgin multilayer tape and the second layer of the virgin multilayer tape are dragged in the divergent directions, thereby separating the first layer of the virgin multilayer tape and the second layer of the virgin multilayer tape. In this way, the first layer of the virgin multilayer tape is separated from the second layer of the virgin multilayer tape, and one of them can be fed to the production line of absorbent articles.

In a second aspect thereof, the present invention relates to an apparatus for feeding a production line of absorbent sanitary articles with a layer of a virgin multilayer tape.

Preferably, a first holding device is provided, the first holding device being configured to hold a head free end of said virgin multilayer tape partially unwound from a respective virgin spool.

Preferably, a second holding device is provided, the second holding device being configured to hold a tail free end of a multilayer tape in use.

Preferably, a first applicator is provided, the first applicator being configured to apply a first connecting element on a first layer of the virgin multilayer tape and on a first layer of the multilayer tape in use at said head free end and tail free end.

Preferably, a second applicator is provided, the second applicator being configured to apply a second connecting element on a second layer of the virgin multilayer tape and on a second layer of the multilayer tape in use at said head free end and tail free end.

Preferably, a first pulling member is provided, the first pulling member being configured to pull the first layer of said virgin multilayer tape in a first direction by making the first layer of the multilayer tape in use and the first connecting element advance in the first direction.

Preferably, a second pulling member is provided, the second pulling member being configured to pull the second layer of said virgin multilayer tape in a second direction by making the second layer of the multilayer tape in use and the second connecting element advance in the second direction.

Preferably, said second direction is divergent from said first direction.

The term "tape" is used to indicate a body having a length, measured along a respective longitudinal direction, a width measured along a respective transverse direction orthogonal to the longitudinal direction and a thickness measured along a respective vertical direction orthogonal to the longitudinal direction and to the transverse direction, wherein the length is greater than the width by at least two orders of magnitude and the thickness is less than the width by at least two orders of magnitude.

The term "free end" of a multilayer tape (virgin or in use) is used to indicate a longitudinal end of the tape, at which the tape has an edge that extends substantially transversely.

The present invention may have, in both aspects discussed above, at least one of the preferred features described below. Such features may thus be present individually or in combination with each other, unless expressly stated otherwise, both in the method of the first aspect of the present invention and in the apparatus of the second aspect of the present invention.

Preferably, the method of the first aspect of the present invention may be implemented by an apparatus in accordance with the second aspect of the present invention.

Preferably, said virgin multilayer tape comprises a first layer and a second layer overlapped to the first layer.

Preferably, the multilayer tape in use comprises a first layer and a second layer overlapped to the first layer.

In a preferred embodiment, such as for example the one shown in the accompanying figures, the layer to be fed to the production line is the second layer of the virgin multilayer tape. In such an embodiment, the second layer of said virgin multilayer tape and of said multilayer tape in use comprises a main layer comprising a glue substrate and the first layer of said virgin multilayer tape and of said multilayer tape in use comprises a protective layer to be removed that covers the glue substrate of the main layer.

In an alternative embodiment, not shown in the accompanying figures, the layer to be fed to the production line is the first layer of the virgin multilayer tape. In such an embodiment, the first layer of said virgin multilayer tape and of said multilayer tape in use comprises a main layer comprising a glue substrate and the second layer of said virgin multilayer tape and of said multilayer tape in use comprises a protective layer to be removed that covers the glue substrate of the main layer.

In a particularly preferred embodiment, the aforesaid main layer defines the covering sheet provided with glue which is intended to be applied to the lower layer of the absorbent sanitary article.

The Applicant has in fact observed that, conventionally, during the production of the absorbent sanitary article, a glue substrate is applied on the lower layer of the absorbent sanitary article or on the covering sheet, and then the covering sheet is applied on the lower layer of the absorbent sanitary article so that the glue substrate remains interposed between the lower layer of the absorbent sanitary article and the covering sheet.

In markets that are more sensitive to environmental issues, lawmakers and consumers prefer biodegradable products.

Sanitary pads of the biodegradable type have recently been made that can be disposed of in the WC bowls of the toilets and be dissolved in water in some days, weeks or months. In these products, the lower layer is made of a biodegradable fibrous material, for example carboxymethylcellulose (CMC).

The Applicant has therefore thought to apply a biodegradable and water-soluble glue on the lower layer of the absorbent sanitary articles.

Typically, the biodegradable glues are water-based and in the liquid state at room temperature, unlike traditional glues which are typically synthetic-based and solid at room temperature.

The Applicant has verified that, if a biodegradable glue is applied in the liquid state on the lower layer of a pad made of a biodegradable fibrous material, the glue is absorbed by the fibrous material, penetrating in the lower layer and significantly worsening the adhesive performance of the adhesive portions. In addition, the glue absorbed by the lower layer risks to stiffen the sanitary pad, worsening the comfort thereof.

The Applicant has perceived that, by allowing the biodegradable glue to partially dry before applying it on the lower layer, the glue is absorbed by the fibrous material in a smaller amount and tends to remain on the surface, maintaining its adhesive performance.

The Applicant has therefore thought that, in order to allow the glue to partially dry before being applied, it is possible to apply the glue substrate on a main layer from which the covering sheets are cut out before application on the lower layer of the absorbent article and to apply on the lower layer of the absorbent article one or more covering sheets on which a partially dried biodegradable glue substrate is already applied.

The Applicant has found that, in order to transport and store the main layer with the glue substrate already applied, it is possible to cover the glue substrate with a removable protective layer and to obtain a multilayer tape that can be wound in spools without ruining the glue substrate. At the time of application, the multilayer tape can be unwound from the spool, the protective layer removed for disposal thereof and the main layer provided with the glue substrate fed to the absorbent article production line, where it is cut to obtain the covering sheets to be applied to the lower layer.

Preferably, applying said second connecting element is performed after having applied said first connecting element.

Preferably, applying said first connecting element is performed while said head free end and tail free end are stationary.

Preferably, said head free end and tail free end are moved after having applied the first connecting element and before applying the second connecting element.

Preferably, the multilayer tape in use and the virgin multilayer tape are made to advance along an advancement path.

Preferably, the apparatus is configured to make said multilayer tape in use and virgin multilayer tape advance along said advancement path.

Preferably, the second connecting element is applied while said head free end and tail free end are moving along the advancement path.

Preferably, said second applicator is arranged downstream of said first applicator along said advancement path.

Preferably, said second applicator is configured to apply said second connecting element subsequently to the first connecting element.

Preferably, said second applicator is configured to apply the second connecting element while said head free end and tail free end are moving along the advancement path.

Preferably, a sensor is provided.

Preferably, the first connecting element already applied is detected by said sensor.

Preferably, the first connecting element is detected while the first connecting element is moving along the advancement path.

Preferably, the sensor is configured to detect the first connecting element applied on the first layer of the virgin multilayer tape and on the first layer of the multilayer tape in use at said head free end and tail free end.

Preferably, the sensor is arranged along the advancement path between the first applicator and the second applicator.

Preferably, applying said second connecting element is performed when the sensor detects the first connecting element.

Preferably, applying said second connecting element is performed at a predetermined time after the sensor detects the first connecting element so that the second connecting element is applied at the first connecting element.

Preferably, said second applicator is configured to apply said second connecting element when the sensor detects the first connecting element.

Preferably, said second applicator is configured to apply said second connecting element at said predetermined time after the sensor detects the first connecting element.

Preferably, said first connecting element and second connecting element, when applied, are not overlapped to each other.

Preferably, applying the first connecting element comprises arranging the head free end of the virgin multilayer tape in a position adjacent to the tail free end of the multilayer tape in use without overlapping the head free end to the tail free end.

Preferably, arranging the head free end of the virgin multilayer tape in a position adjacent to the tail free end of the multilayer tape in use comprises arranging the head free end of the virgin multilayer tape at a distance of less than 5 mm from the tail free end of the multilayer tape in use, said distance preferably being less than 3 mm.

In one embodiment, arranging the head free end of the virgin multilayer tape in a position adjacent to the tail free end of the multilayer tape in use comprises arranging the head free end of the virgin multilayer tape in contact with the tail free end of the multilayer tape in use, without overlapping them.

In one embodiment, applying the first connecting element on the first layer of the virgin multilayer tape and on the first layer of the multilayer tape in use comprises applying said first connecting element simultaneously to the first layer of the virgin multilayer tape and to the first layer of the multilayer tape in use.

In another embodiment, applying the first connecting element comprises applying said first connecting element only to the first layer of the virgin multilayer tape at said head free end, moving said first connecting element and head free end of the virgin multilayer tape towards the tail free end of the multilayer tape in use, and subsequently applying said first connecting element to the first layer of the multilayer tape in use at said tail free end.

Preferably, by feeding the main layer of the virgin multilayer tape to the absorbent sanitary article production line, the virgin spool becomes a spool in use.

Preferably, the method in accordance with the first aspect i repeated each time the spool in use is running out.

Preferably, at each iteration subsequent to the first one of the method in accordance with the first aspect, applying the first connecting element on the first layer of the virgin multilayer tape and on the first layer of the multilayer tape in use comprises applying said first connecting element simultaneously to the first layer of the virgin multilayer tape and to the first layer of the multilayer tape in use if, at the previous iteration, applying the first connecting element comprises applying said first connecting element only to the first layer of the virgin multilayer tape at said head free end, moving said first connecting element and head free end of the virgin multilayer tape towards the tail free end of the multilayer tape in use, and subsequently applying said first connecting element to the first layer of the multilayer tape in use at said tail free end.

Preferably, at each iteration subsequent to the first one of the method in accordance with the first aspect, applying the first connecting element on the first layer of the virgin multilayer tape and on the first layer of the multilayer tape in use comprises applying said first connecting element only to the first layer of the virgin multilayer tape at said head free end, moving said first connecting element and head free end of the virgin multilayer tape towards the tail free end of the multilayer tape in use, and subsequently applying said first connecting element to the first layer of the multilayer tape in use at said tail free end, if, at the previous iteration, applying the first connecting element comprises applying said first connecting element simultaneously to the first layer of the virgin multilayer tape and to the first layer of the multilayer tape in use.

In one embodiment, applying said first connecting element comprises pressing the first applicator against said head free end and said first holding device.

Preferably, applying said first connecting element comprises pressing the first applicator against said tail free end and said second holding device.

Preferably, applying said second connecting element comprises pressing a second applicator against said head free end and tail free end and against an opposing abutment element.

Preferably, said first applicator and said second applicator are arranged on opposite sides of said advancement path.

Preferably, applying said first connecting element comprises holding said first connecting element on said first applicator while said first applicator is moved towards said head free end and tail free end.

Preferably, applying said second connecting element comprises holding said second connecting element on said second applicator while said second applicator is moved towards said head free end and tail free end.

Preferably, said first connecting element comprises at least one adhesive sheet.

Preferably, said second connecting element comprises at least one adhesive sheet.

Preferably, providing the tail free end of said multilayer tape in use comprises at least partially unwinding the multilayer tape in use from a respective spool in use and transversely cutting the multilayer tape in use.

Preferably, a knife configured to transversely cut the multilayer tape in use is provided.

Preferably, providing the head free end of said virgin multilayer tape comprises holding the head free end with a first holding device.

Alternatively, providing the head free end of said virgin multilayer tape comprises holding the head free end on the first applicator.

Preferably, providing the tail free end of said multilayer tape in use comprises holding the tail free end with a second holding device.

Preferably, said first applicator is movable between a respective rest position and a respective application position.

Preferably, said second applicator is movable between a respective rest position and a respective application position.

Preferably, said first and/or second pulling member comprises at least one aspirated motorized roller.

Preferably, the sensor controls the movement of the second applicator.

Preferably, said first holding device and second holding device are configured to align said head free end and tail free end along a common lying plane.

Preferably, said first applicator and second applicator are configured to move between the respective rest and application positions on opposing parts with respect to said advancement path.

BRIEF DESCRIPTION OF THE DRAWINGS

Further characteristics and advantages of the present invention will become clearer from the following detailed description of a preferred embodiment thereof, made with reference to the appended drawings and provided by way of indicative and non-limiting example, in which.

DETAILED DESCRIPTION

Figure 1:
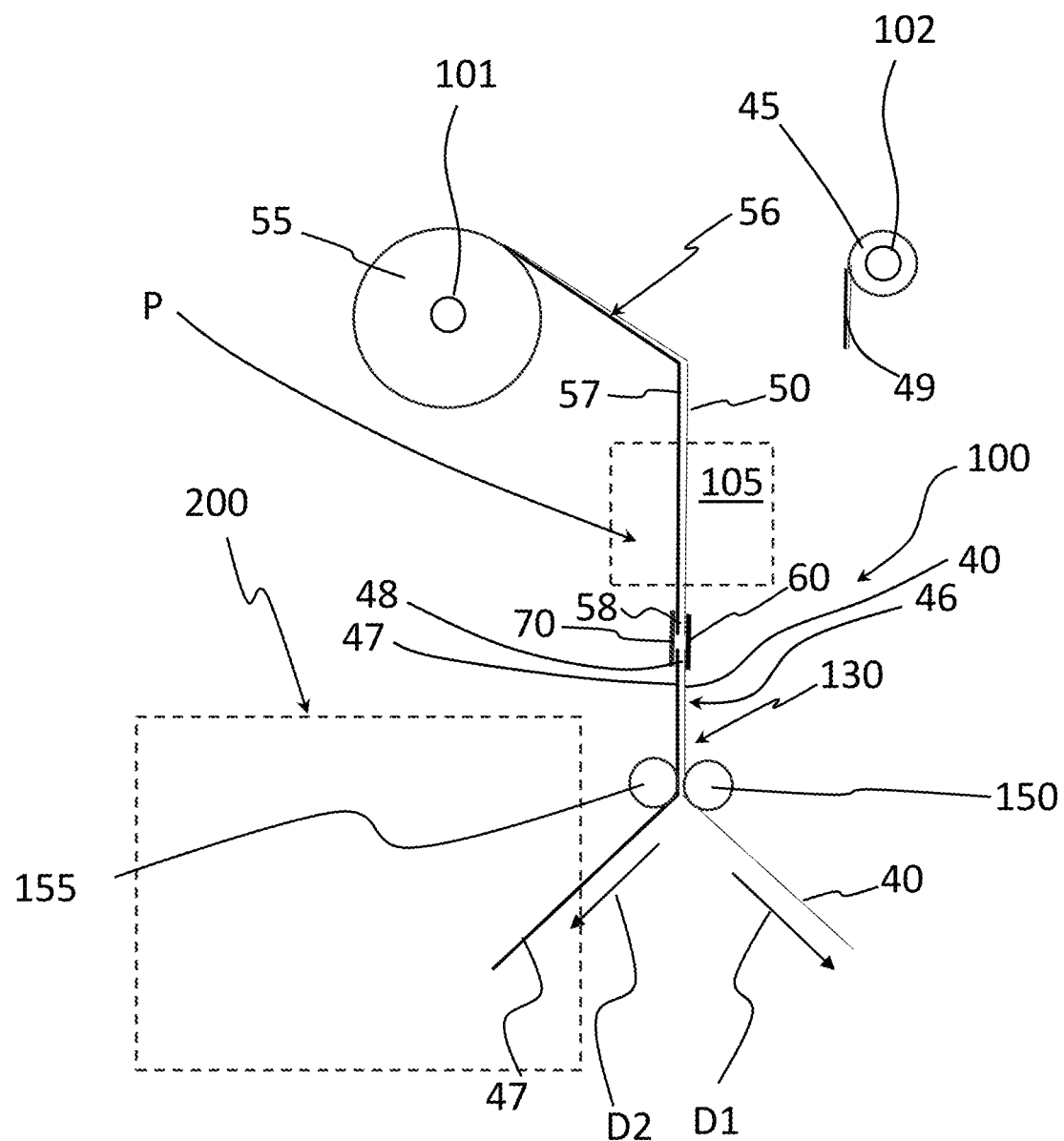
FIG. 1 is a schematic view of an apparatus in accordance with the present invention.

In the accompanying figures, the reference numeral 100 is used to indicate an apparatus in accordance with the present invention. The apparatus 100 is configured to feed a production line 200 of absorbent sanitary article (schematically shown in FIG. 1) with a main layer 47 of a multilayer tape in use 46 and, subsequently, with a main layer 57 of a virgin multilayer tape 56.

In a preferred embodiment thereof, each main layer 47, 57 comprises a main substrate made of a solid material, preferably at least partially biodegradable, for example paper, and a glue substrate that covers the main substrate.

In the production line 200, not shown in detail, a plurality of semi-finished products of absorbent sanitary articles are being processed. The main layer 47 and thereafter the main layer 57 are continuously fed from the apparatus 100 to the production line 200, where they are cut into discrete sheets (not shown) of rectangular or square shape, each comprising a portion of the main substrate covered with a portion of the glue substrate.

Non-limiting examples of absorbent sanitary articles made in the production line 200 are sanitary pads for women, baby diapers, diapers and pads for people suffering from incontinence and the like. Such absorbent sanitary articles (not shown) comprise an upper layer and a lower layer overlapped and joined together, between which a core of absorbent material is interposed. The lower layer is made of a non-woven fabric, preferably of biodegradable cellulose-based material.

In the production line 200, one or more discrete sheets obtained by cutting the main layers 47, 57 are applied to each semi-finished product of absorbent article, so that the glue of the respective glue substrate adheres to the lower layer and remains stuck on the surface of the lower layer. The glue of each glue substrate is viscous enough to remain on the surface and not penetrate in a significant amount into the lower layer.

Each main substrate is configured such that the portion of main substrate of each discrete sheet is weakly held on the lower layer of the absorbent article by the glue of the respective glue substrate and performs the function of protecting the glue. The absorbent sanitary articles are then packaged with the respective main substrates still held on the lower layer, so that they can be removed by the end consumer at the time of use of the absorbent sanitary article.

Each main layer 47, 57 is stored, transported and preserved in a respective spool 45, 55. A respective multilayer tape 46, 56 is wound on each spool 45, 55. In FIG. 1, the multilayer tape 46, hereinafter referred to as "multilayer tape in use", has been unwound from the spool 45, hereinafter referred to as "spool in use", and made to advance along an advancement path P to feed the main layer 47 to the production line 200 and the multilayer tape 56, hereinafter referred to as "virgin multilayer tape" is unwound from the spool 55, hereinafter referred to as "virgin spool", and made to advance along the advancement path P to feed the main layer 57 to the production line 200 upon depletion of the main layer 47.

Each multilayer tape 46, 56 comprises the respective main layer 47, 57 and a respective protective layer 40, 50 overlapped to the glue substrate of the respective main layer 47, 57 to protect the glue substrate. Each protective layer 40, 50 is configured to be interposed between successive overlapped windings of the main layer 47, 57 of the respective multilayer tape 46, 56 wound on the respective spool 45, 55, so as to prevent these successive windings from sticking together due to the glue substrate.

Each protective layer 40, 50 is made of a material that can adhere to the glue substrate and be easily removed leaving the glue on the respective main substrate. Each protective layer 40, 50 is configured so that it can be removed from the respective main layer 47, 57 without dragging the glue away from the glue substrate. The protective layers 40, 50 are for example made of siliconized paper. The main layer 47 and the protective layer 40 overlapped thereon form the multilayer tape 46 and are wound together on the spool 45. The main layer 57 and the protective layer 50 overlapped thereon form the multilayer tape 56 and are wound together on the spool 55.

The apparatus 100 comprises a first spool support 101 and a second spool support 102 configured to interchangeably support the spools 45 and 55.

Figure 2:
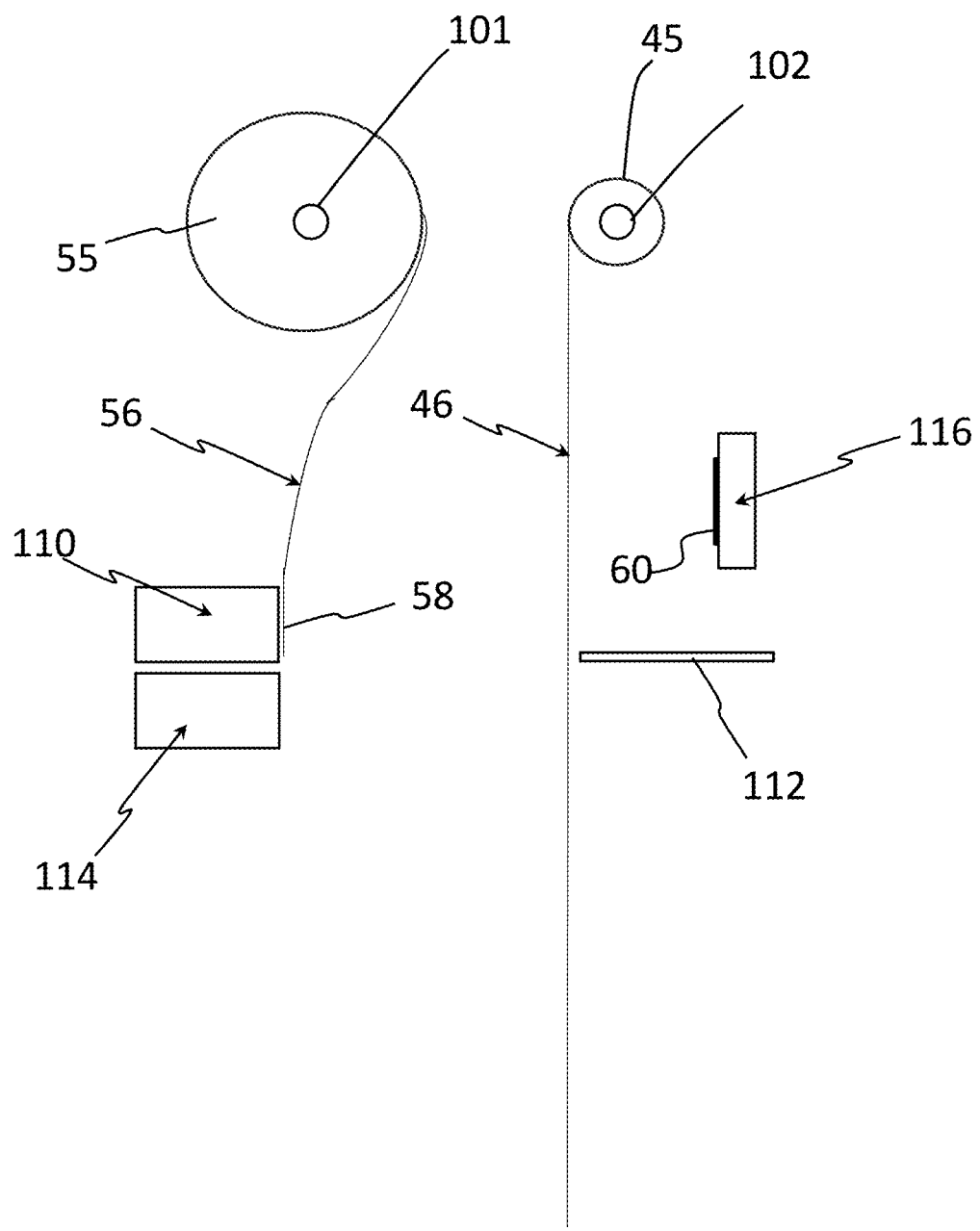
FIGS. 2-7 are schematic views of details of the apparatus of FIG. 1, in respective operating configurations in accordance with the method of the present invention.
Figure 3:
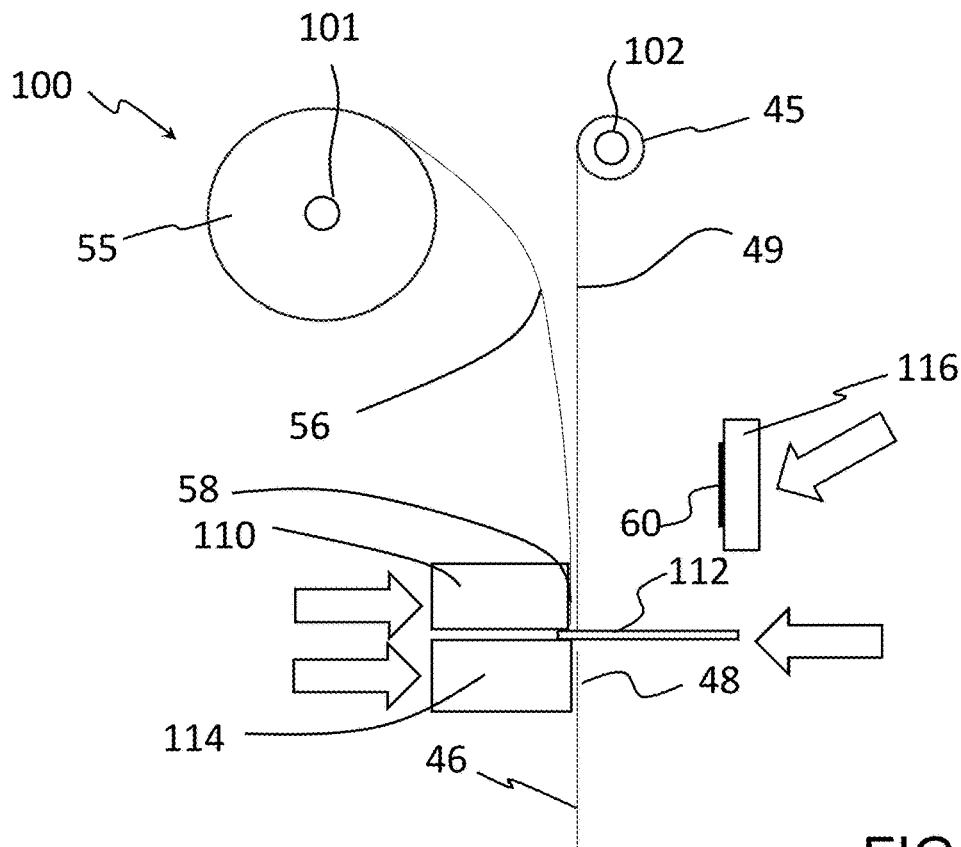

In a first operating configuration of the apparatus 100, shown in FIGS. 1-3, the second spool support 102 supports the spool in use 45, whose multilayer tape in use 46 has been unwound to feed its main layer 47 to the production line 200. In this operating configuration the first spool support 101 is available for receiving the virgin spool 55 so that the virgin spool 55 is ready to replace the spool in use 45 when the latter is depleted.

Figure 9:
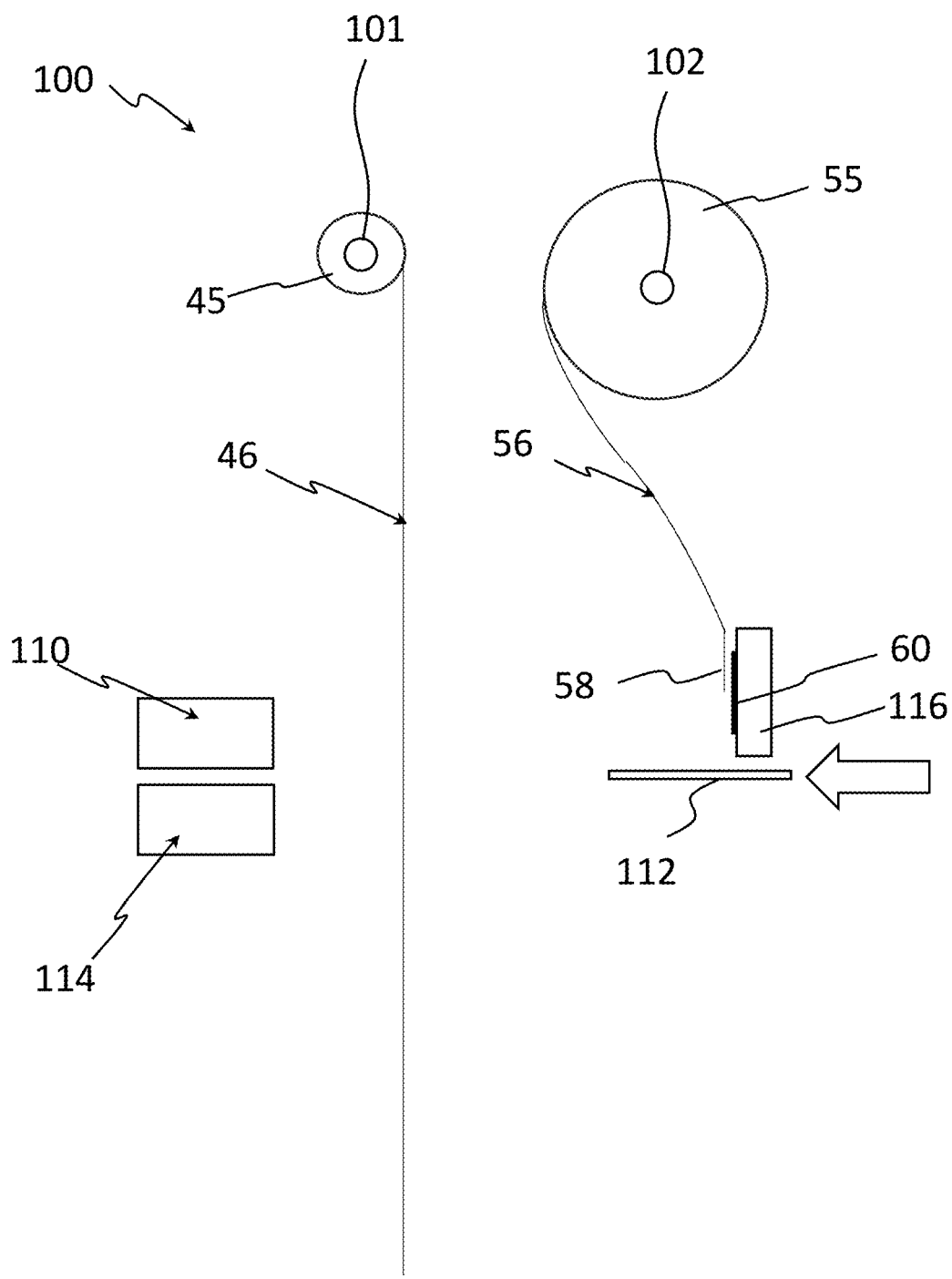
FIGS. 9-11 are schematic views of details of the apparatus of FIG. 1, in further operating configurations in accordance with the method of the present invention.
Figure 10:
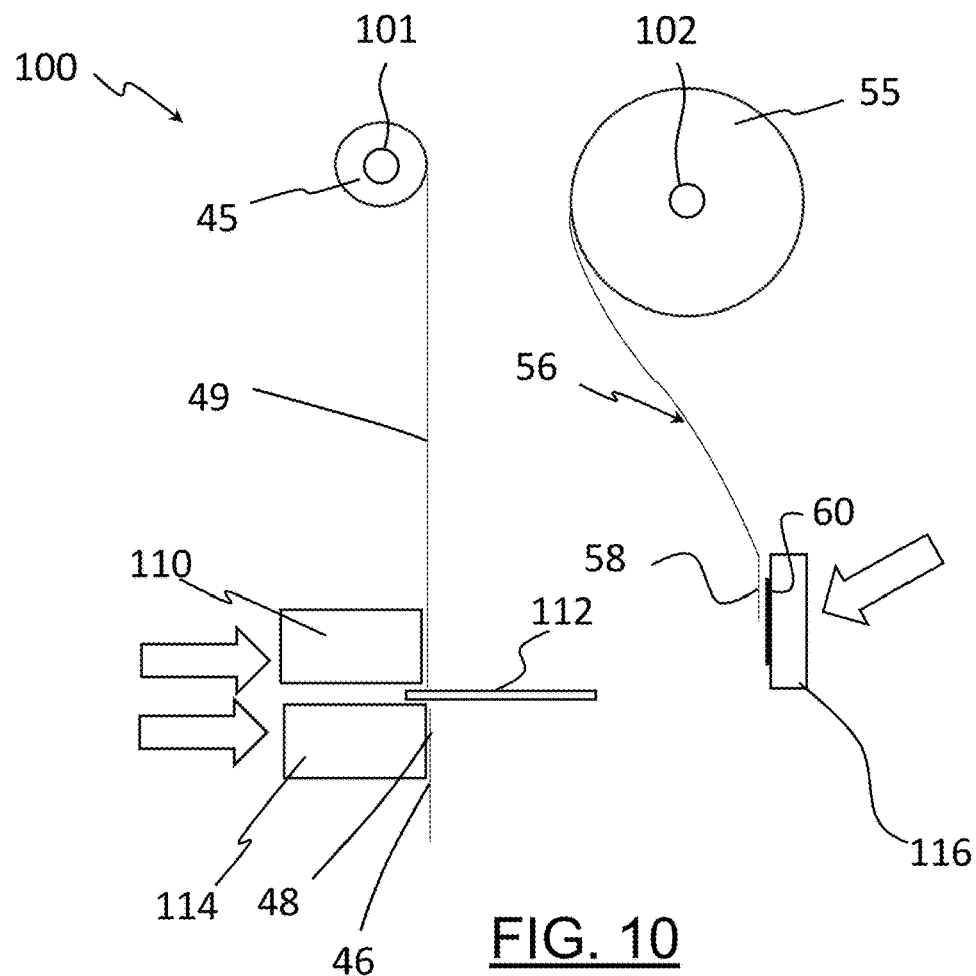
Figure 11:
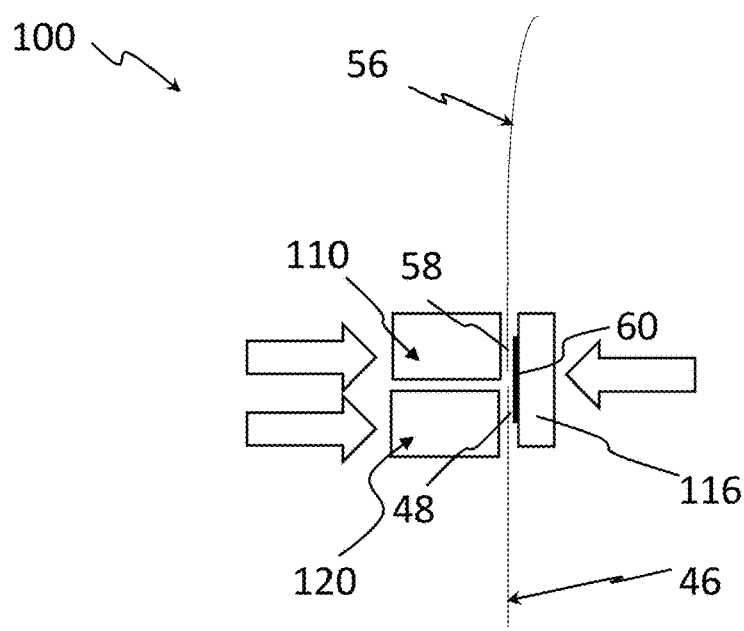

In a second operating configuration of the apparatus 100, shown in FIGS. 9 and 10, the first spool support 101 supports the spool in use 45 while the main layer 47 of the multilayer tape in use 46 is fed to the production line 200. In the second configuration the second spool support 102 is available for receiving the virgin spool 55, so that the virgin spool 55 is ready to replace the spool in use 45 when the latter is depleted.

In this way the virgin multilayer tape 56 of the virgin spool 55 can be replaced quickly to the multilayer tape in use 46 after depletion of the multilayer tape in use 46.

The apparatus 100 comprises a joining station 105, schematically shown in FIG. 1, at which the virgin multilayer tape 56 is joined to the multilayer tape in use 46.

Figure 4:
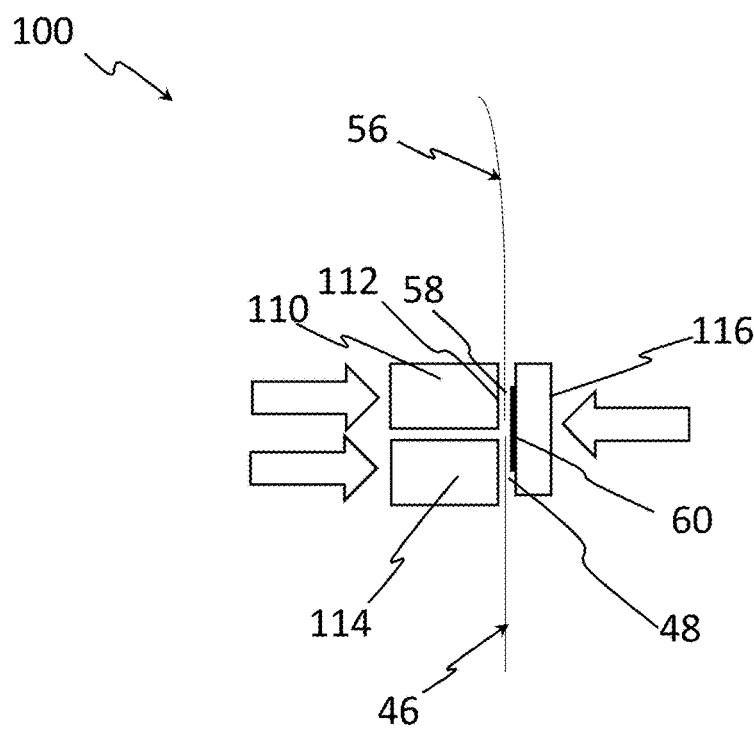
Figure 5:
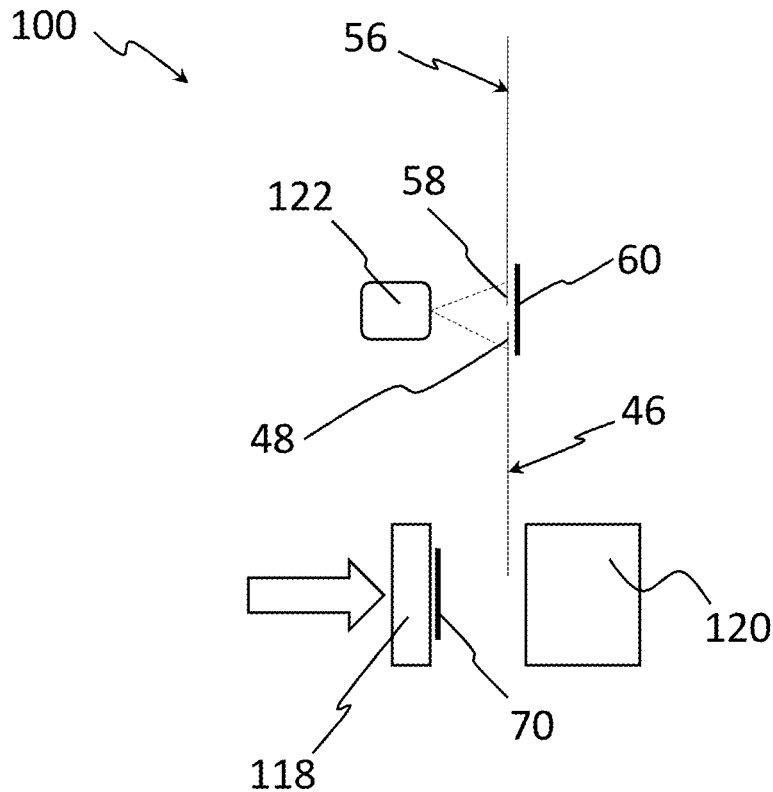
Figure 6:
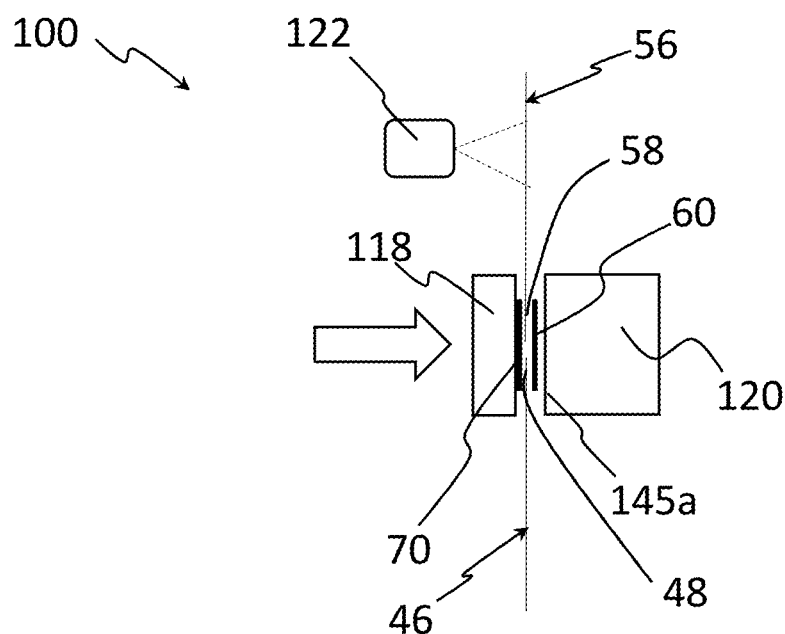

The joining station 105 comprises a first holding device 110. The first holding device 110 is configured to hold a head free end 58 of the virgin multilayer tape 56, partially unwound from the virgin spool 55 (FIG. 4). The head free end 58 of the virgin multilayer tape 56 can be positioned on the first holding device 110 manually by an operator. The first holding device 110 is preferably pneumatic and is configured to hold the head free end 58 by suction. The first holding device 110 is configured to hold the head free end 58 of the virgin multilayer tape 56 in the first configuration of the apparatus 100. The head free end 58 of the virgin multilayer tape 56 is arranged on the first holding device 110 with the main layer 57 placed against the first holding device 110 and the protective layer 50 facing away from the first holding device 110.

The joining station 105 further comprises a knife 112. The knife 112 is configured to cut the multilayer tape in use 46 to obtain a tail free end 48. In the first operating configuration and in the second operating configuration of the apparatus 100, when the spool in use 45 is running out, the multilayer tape in use 46 is stopped and held under tension and the knife 112 traverses the multilayer tape in use 46 to cut it clean transversely. The cut part 49 of the multilayer tape in use 46 that remains partially wound in the spool in use 45 is disposed of.

The joining station 105 further comprises a second holding device 114. The second holding device 114 is configured to hold the tail free end 48 of the multilayer tape in use 46. The second holding device 114 is adjacent to the first holding device 110. The second holding device 114 is configured to hold the tail free end 48 of the multilayer tape in use 46 cut by the knife 112. The second holding device 114 is preferably pneumatic and is configured to hold the tail free end 48 by suction. The first holding device 110 and the second holding device 114 have a common lying plane. In the first and second operating configurations, the first holding device 110 and the second holding device 114 hold the multilayer tape in use 46 while it is cut by the knife 112 and, subsequently, the second holding device 114 holds the tail free end 48 of the multilayer tape in use 46. After cutting, the tail free end 48 of the multilayer tape in use 46 is arranged on the second holding device 114 with the protective layer 40 and the main layer 47 arranged as the virgin multilayer tape 56. The main layer 47 is placed against the second holding device 114 and the protective layer 40 faces away from the second holding device 114.

The joining station 105 further comprises a first applicator 116. The first applicator 116 is configured to hold a first connecting element 60 and to apply it on the protective layer 50 of the virgin multilayer tape 56 and on the protective layer 40 of the multilayer tape in use 46 at the head free end 58 and the tail free end 48. The first connecting element 60 comprises an adhesive sheet 61 having an adhesive face and a non-adhesive face. The first applicator 116 is arranged on the opposite side to the first holding device 110 and the second holding device 114 with respect to the advancement path P.

The first applicator 116 is configured to hold the first connecting element 60 by suction from the side of the non-adhesive face. The first applicator 116 is movable between a rest position distal with respect to the first holding device 110 and to the second holding device 114 and an application position proximal and facing the first holding device 110 and the second holding device 114. The first applicator 116, in the respective application position, is configured to press the adhesive face of the first connecting element 60 against the first holding device 110 and the second holding device 114.

In the first configuration of the apparatus 100, the first connecting element 60 is arranged on the first applicator 116 in the rest position, preferably manually by the operator. After the knife 112 has cut the multilayer tape in use 46, the tail free end 48 of the multilayer tape in use 46 is held by the second holding device 114 and the head free end 58 of the virgin multilayer tape 56 is held by the first holding device 110, the one next to the other and in a common lying plane. The first applicator 116 is moved from the rest position to the application position towards the first holding device 110 and the second holding device 114. In the application position, the adhesive face of the first connecting element 60 contacts the head free end 58 and the tail free end 48, adhering to both. The first holding device 110 and the second holding device 114 hold the tail free end 48 of the multilayer tape in use 46 and the head free end 58 of the virgin multilayer tape 56 from opposite the side to the first applicator 116 during application of the first connecting element 60. The first applicator 116 is then returned to the rest position.

In the second configuration of the apparatus 100, the first connecting element 60 is preliminarily applied to the head free end 58 of the virgin multilayer tape 56 partially unwound from the virgin spool 55, preferably manually by an operator, so as to protrude from the head free end 58. The first connecting element 60 and the head free end 58 are then both arranged, already joined, on the first applicator 116 in the rest position, preferably manually by the operator. After the knife 112 has cut the multilayer tape in use 46, the tail free end 48 of the multilayer tape in use 46 is held by the second holding device 114. The first applicator 116 is moved from the rest position to the application position towards the first holding device 110 and the second holding device 114. In the application position, the adhesive face of the first connecting element 60 protruding from the head free end 58 of the virgin multilayer tape 56 contacts the tail free end 48 of the multilayer tape in use 46, adhering thereto. The first applicator 116 is then returned to the rest position. The first connecting element 60 is applied on the protective layer 50 of the virgin multilayer tape 56 and on the protective layer 40 of the multilayer tape in use 46 to join the protective layers 50, 40 of the virgin multilayer tape 56 and of the multilayer tape in use 46. In this way the multilayer tape in use 46 and the virgin multilayer tape 56 are joined together through the respective protective layers 40, 50.

The joining station 105 further comprises a second applicator 118. The second applicator 118 is configured to hold a second connecting element 70 and to apply it on the main layer 57 of the virgin multilayer tape 56 and on the main layer 47 of the multilayer tape in use 46 at the head free end 58 and the tail free end 48. The second applicator 118 is arranged downstream of the first applicator 116 along the advancement path P. The second applicator 118 is further arranged on the opposite side to the first applicator 116 with respect to the advancement path P.

The second connecting element 70 comprises one or more adhesive sheets 71 having an adhesive face and a non-adhesive face. The second applicator 118 is analogous to the first applicator 116. The second applicator 118 is configured to hold the second connecting element 70 by suction from the side of the non-adhesive face.

The joining station 105 also comprises an abutment element 120. The abutment element 120 is arranged on the opposite side to the second applicator 118 with respect to the advancement path P. The second applicator 118 is movable between a rest position distal with respect to the abutment element 120 and an application position proximal and facing the abutment element 120. The second applicator 118, in the respective application position, is configured to press the adhesive face of the second connecting element 70 against the abutment element 120.

The joining station 105 also comprises a sensor 122. The sensor 122 is arranged along the advancement path P between the first applicator 116 and the second applicator 118. The sensor 122 is arranged downstream of the first applicator 116 and upstream of the second applicator 118 with respect to the advancement path P. The sensor 122 is configured to detect the first connecting element 60. Preferably, the sensor 122 is of the optical type, for example a photocell, and faces toward the advancement path P.

In both the first configuration and the second configuration of the apparatus 100, the second connecting element 70 is arranged on the second applicator 118 in a rest position, preferably manually by the operator.

The second connecting element 70 is applied on the second applicator 118 such that it is not overlapped to the first connecting element 60 when applied. For example, as shown in FIG. 9, the first connecting element 60 may comprise a single adhesive sheet 61 positioned on the first applicator 116 so as to be applied at a central portion of the head free end 58 and tail free end 48 and the second connecting element 70 may comprise two adhesive sheets 71 positioned on the second applicator 118 so as to be applied at opposite side portions of the head free end 58 and of the tail free end 48, to the sides of the first connecting element 60, or vice versa. In a further example that is non shown, the first connecting element 60 may comprise a single adhesive sheet positioned on the first applicator 116 so as to be applied at a side portion of the head free end 58 and tail free end 48 and the second connecting element 70 may comprise a single sheet positioned on the second applicator 118 so as to be applied at an opposite side portion of the head free end 58 and of the tail free end 48.

The second applicator 118 is controlled by signals received by the sensor 122, so as to apply the second connecting element 70 on the head free end 58 and tail free end 48 at the first connecting element 60. After the first applicator 116 has applied the first connecting element 60, the multilayer tape in use 46 and the virgin multilayer tape 56 are made to advance along the advancement path P joined by only the first connecting element 60 at the respective head free end 58 and tail free end 48. The second connecting element 70 is applied subsequently to the first connecting element 60, while the head free end 58 and tail free end 48 are moving along the advancement path P. The sensor 122 detects the first connecting element 60 and controls the movement of the second applicator 118 from the rest position to the application position. The movement of the second applicator 118 from the moment in which the sensor 122 detects the first connecting element 60 can be substantially instantaneous or delayed by a pre-established time so that the second connecting element 70 is applied at the first connecting element 60. In the application position, the adhesive face of the second connecting element 70 contacts the head free end 58 and the tail free end 48, adhering to both. The abutment element 120 holds the tail free end 48 of the multilayer tape in use 46 and the head free end 58 of the virgin multilayer tape 56 on the side opposite to the second applicator 118 during application of the first connecting element 60. The second applicator 118 is then returned to the rest position.

The second connecting element 70 is applied on the main layer 57 of the virgin multilayer tape 56 and on the main layer 47 of the multilayer tape in use 46 to join the main layers 57, 47 of the virgin multilayer tape 56 and of the multilayer tape in use 46. In this way, the second connecting element 70 joins the multilayer virgin tape 56 to the multilayer tape in use 46 on the opposite side to the first connecting element 60 and through the respective main layers 57, 47.

Figure 7:
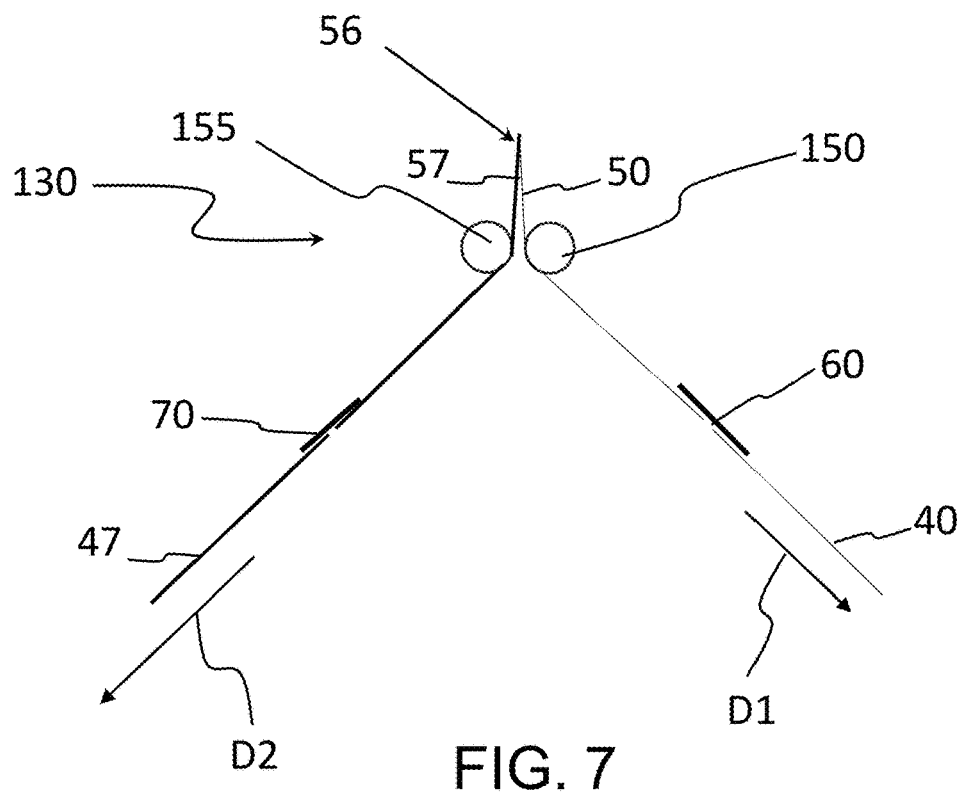
Figure 8:
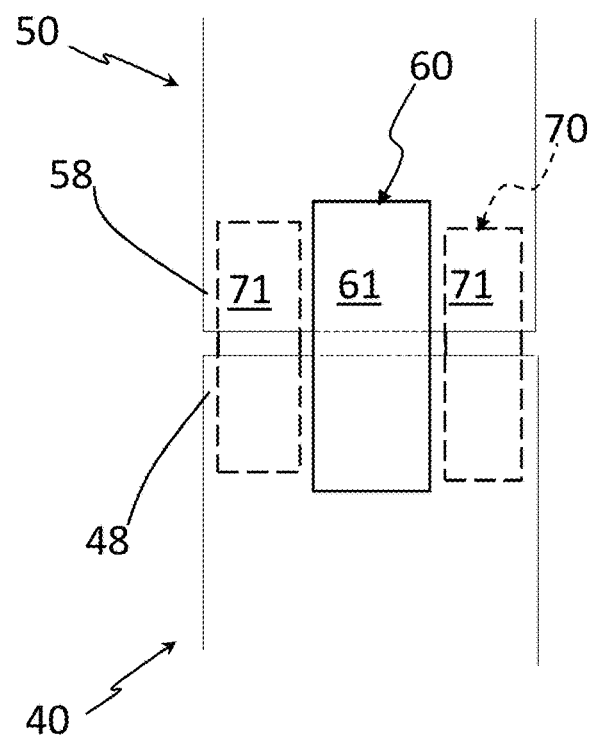
FIG. 8 is a schematic plan view of two joined tapes in accordance with the method of the present invention.

A separation station 130, shown in FIGS. 1 and 7, is arranged downstream of the joining station 105 along the advancement path P. In the separation station 130 the protective layer 40 is separated from the main layer 47.

A first pulling member 150 is arranged at the separation station 130. The first pulling member 150 is configured to move the protective layer 40 of the multilayer tape in use 46 and the protective layer 50 of the virgin multilayer tape 56 in a first direction D1. In the accompanying figures, the first pulling member 150 is schematically represented as a roller.

A second pulling member 155 is arranged at the separation station 130. The second pulling member 155 is configured to move the main layer 47 of the multilayer tape in use 46 and the main layer 57 of the virgin multilayer tape 56 in a second direction D2. The second direction D2 is divergent from the first direction D1. In the accompanying figures the second pulling member 155 is schematically represented as a roller.

After the application of the first connecting element 60 and of the second connecting element 70, the first pulling member 150 and the second pulling member 155 move the protective layer 40 and the main layer 47 of the multilayer tape in use 46 respectively in the first direction D1 and in the second direction D2. The tail free end 48 of the multilayer tape in use 46, the first connecting element 60, the second connecting element 70, and the head free end 58 of the multilayer tape in use 46 are dragged along the advancement path P towards the separation station 130.

When the tail free end 48 of the multilayer tape in use 46 arrives at the separation station 130, the first connecting element 60 is dragged in the first direction D1 by the protective layer 40 of the multilayer tape in use 46. The first connecting element 60 in turn drags in the first direction D1 the protective layer 50 of the virgin multilayer tape 56. At the same time, the second connecting element 70 is dragged in the second direction D2 by the main layer 47 of the multilayer tape in use 46. The second connecting element 70 in turn drags in the second direction D2 the main layer 57 of the virgin multilayer tape 56.

In the embodiment shown in the figures, the protective layer 40 of the multilayer tape in use 46 and the protective layer 50 of the virgin multilayer tape 56, after the separation of the main layers 40 and 50, are conveyed to a disposal device 140. The main layer 47 of the multilayer tape in use 46 and the main layer 57 of the virgin multilayer tape 56, after the separation of the protective layers 40 and 50, are conveyed to the production line 200.

In the disposal device 140, the protective layer is disposed of, e.g. destroyed.

The main layer 57 of the virgin multilayer tape 56 is fed to the production line 200. The virgin multilayer tape 56 thus becomes the multilayer tape in use 46 and the virgin spool 55 from which it is unwound becomes the spool in use 45. When such a spool is running out, the method described above may be repeated. The method is repeated by alternating at each iteration the first operating configuration and the second operating configuration of the apparatus 100 described above.

Obviously, a person skilled in the art, in order to satisfy specific and contingent needs, can make numerous modifications and changes to the invention described above while remaining within the scope of protection defined by the following claims.

The invention claimed is:

1. A method for feeding a production line of absorbent sanitary articles with a layer of a virgin multilayer tape, comprising:
   providing a head free end of said virgin multilayer tape partially unwound from a respective virgin spool;
   providing a tail free end of a multilayer tape in use;
   applying a first connecting element on a first layer of the virgin multilayer tape and on a first layer of the multilayer tape in use at said head free end and said tail free end;
   applying a second connecting element on a second layer of the virgin multilayer tape and on a second layer of the multilayer tape in use at said head free end and said tail free end;
   pulling the first layer of said virgin multilayer tape in a first direction (D1) by making the first layer of the multilayer tape in use and the first connecting element advance in the first direction (D1);
   pulling the second layer of said virgin multilayer tape in a second direction (D2) divergent from the first direction by making the second layer of the multilayer tape in use and the second connecting element advance in the second direction.

2. The method according to claim 1, wherein the layer to be fed to the production line is the second layer of the virgin multilayer tape, wherein each of the second layer of the virgin multilayer tape and the second layer of the multilayer tape in use comprises a main layer comprising a glue substrate, and wherein each of the first layer of the virgin multilayer tape and the first layer of the multilayer tape in use comprises a protective layer to be removed that covers the glue substrate of the main layer.

3. The method according to claim 2, wherein applying said second connecting element is performed after applying said first connecting element.

4. The method according to claim 1, wherein applying said second connecting element is performed after applying said first connecting element.

5. The method according to claim 4, comprising:
   moving said head free end and said tail free end after applying the first connecting element and before applying the second connecting element;
   wherein the second connecting element is applied while said head free end and said tail free end are moving along a feed path.

6. The method according to claim 5, wherein applying the second connecting element comprises:
   detecting by a sensor the first connecting element already applied;
   wherein applying said second connecting element is performed when the sensor detects the first connecting element.

7. The method according to claim 4, wherein applying the second connecting element comprises:
   detecting by a sensor the first connecting element already applied;
   wherein applying said second connecting element is performed when the sensor detects the first connecting element.

8. The method according to claim 1, wherein said first connecting element and the second connecting element, when applied, are not overlapped to each other.

9. The method according to claim 1, wherein applying the first connecting element comprises arranging the head free end of said virgin multilayer tape in a position adjacent to the tail free end of said multilayer tape in use without overlapping said head free end to said tail free end.

* * * * *